US009541098B2

(12) United States Patent
Duquette (10) Patent No.: US 9,541,098 B2
(45) Date of Patent: Jan. 10, 2017

(54) LOW-NOISE BLOWER

(71) Applicant: CareFusion 303, Inc., San Diego, CA (US)

(72) Inventor: Steven Duquette, Laguna Niguel, CA (US)

(73) Assignee: VYAIRE MEDICAL CAPITAL LLC, Yorba Linda, CA (US)

( * ) Notice: Subject to any disclaimer, the term of this patent is extended or adjusted under 35 U.S.C. 154(b) by 573 days.

(21) Appl. No.: 13/931,465

(22) Filed: Jun. 28, 2013

(65) Prior Publication Data

US 2015/0003966 A1    Jan. 1, 2015

(51) Int. Cl.
| | |
|---|---|
| *F04D 29/30* | (2006.01) |
| *F04D 29/44* | (2006.01) |
| *F04D 29/66* | (2006.01) |
| *F04D 29/28* | (2006.01) |
| *F04D 29/42* | (2006.01) |
| *F04D 29/24* | (2006.01) |
| *F04D 29/40* | (2006.01) |
| *A61M 16/00* | (2006.01) |

(52) U.S. Cl.
CPC ........ *F04D 29/668* (2013.01); *A61M 16/0066* (2013.01); *F04D 29/242* (2013.01); *F04D 29/281* (2013.01); *F04D 29/30* (2013.01); *F04D 29/403* (2013.01); *F04D 29/4226* (2013.01); *F04D 29/664* (2013.01); *A61M 2205/42* (2013.01); *F05D 2240/303* (2013.01); *F05D 2240/307* (2013.01); *F05D 2260/961* (2013.01)

(58) Field of Classification Search
CPC .. F04D 29/664; F04D 29/4226; F04D 29/403; F04D 29/281; F04D 29/282; F04D 29/30; F04D 29/242; F04D 29/441; F05D 2240/303; F05D 2240/307; F05D 2260/961

See application file for complete search history.

(56) References Cited

U.S. PATENT DOCUMENTS

| | | | | |
|---|---|---|---|---|
| 2,037,880 | A | * | 4/1936 | Charavay .............. F04D 29/282 415/213.1 |
| 2,510,125 | A | | 6/1950 | Meakin |
| 2,634,311 | A | | 4/1953 | Darling |
| 3,140,042 | A | * | 7/1964 | Fujii ..................... F04D 29/282 416/186 R |
| 3,673,541 | A | | 6/1972 | Volinskie |

(Continued)

FOREIGN PATENT DOCUMENTS

| | | |
|---|---|---|
| CN | 101687086 A | 3/2010 |
| CN | 202366282 U | 8/2012 |

(Continued)

OTHER PUBLICATIONS

International Search Report and Written Opinion in PCT Application No. PCT/US2014/044438 dated Oct. 28, 2014, 11 pages.

(Continued)

*Primary Examiner* — Ninh H Nguyen
(74) *Attorney, Agent, or Firm* — McDermott Will & Emery LLP (57) ABSTRACT

A low-noise blower has an impeller with an impeller plate and a plurality of blades each attached to the impeller plate. Each blade has a tip and a leading surface with a first portion that is proximate to the tip and has a first radius that is within a range of 0.03-0.20 inch.

20 Claims, 6 Drawing Sheets

(56) References Cited

U.S. PATENT DOCUMENTS

| | | | |
|---|---|---|---|
| 3,776,215 A | 12/1973 | Howard et al. | |
| 3,788,765 A * | 1/1974 | Rusak | F04D 29/284 415/224.5 |
| 4,167,369 A * | 9/1979 | Ishihara | F04D 29/30 416/183 |
| 4,243,357 A * | 1/1981 | Flynn | F01D 5/048 415/218.1 |
| 4,543,041 A | 9/1985 | French et al. | |
| 4,562,744 A | 1/1986 | Hall et al. | |
| 4,571,801 A | 2/1986 | Ewing | |
| 4,754,651 A | 7/1988 | Shortridge et al. | |
| 4,809,742 A | 3/1989 | Grau | |
| 4,825,904 A | 5/1989 | Grau et al. | |
| 4,909,545 A | 3/1990 | Hohol | |
| 4,978,281 A * | 12/1990 | Conger, IV | F04D 25/082 264/271.1 |
| 5,064,346 A | 11/1991 | Atarashi et al. | |
| 5,127,400 A | 7/1992 | DeVries et al. | |
| 5,265,594 A | 11/1993 | Olsson et al. | |
| 5,277,196 A | 1/1994 | Hankinson et al. | |
| 5,295,397 A | 3/1994 | Hall et al. | |
| 5,331,995 A | 7/1994 | Westfall et al. | |
| 5,339,807 A | 8/1994 | Carter | |
| 5,365,795 A | 11/1994 | Brower, Jr. | |
| 5,461,932 A | 10/1995 | Hall et al. | |
| 5,478,206 A * | 12/1995 | Prahst | F04D 29/281 416/186 R |
| 5,537,992 A | 7/1996 | Bjoernstijerna et al. | |
| 5,572,992 A | 11/1996 | Kankkunen et al. | |
| 5,604,681 A | 2/1997 | Koeninger | |
| 5,606,236 A | 2/1997 | Tennies et al. | |
| 5,771,884 A | 6/1998 | Yarnall et al. | |
| 5,918,596 A | 7/1999 | Heinonen | |
| 5,954,051 A | 9/1999 | Heinonen et al. | |
| 6,017,315 A | 1/2000 | Starr et al. | |
| 6,139,262 A * | 10/2000 | Ravidranath | F04D 29/464 415/126 |
| 6,151,557 A | 11/2000 | Broden et al. | |
| 6,422,092 B1 | 7/2002 | Morrison et al. | |
| 6,553,923 B2 * | 4/2003 | Gatley, Jr. | F04D 29/4226 110/162 |
| 6,578,818 B1 | 6/2003 | Krimmer et al. | |
| 6,609,431 B1 | 8/2003 | Tietsworth et al. | |
| 6,622,724 B1 | 9/2003 | Truitt et al. | |
| 6,820,620 B2 | 11/2004 | Rochat | |
| 6,945,123 B1 | 9/2005 | Kuehl et al. | |
| 8,504,318 B2 | 8/2013 | Mendelson et al. | |
| 2002/0085952 A1 | 7/2002 | Ellingboe et al. | |
| 2002/0198668 A1 | 12/2002 | Lull et al. | |
| 2003/0106554 A1 | 6/2003 | de Silva et al. | |
| 2003/0220605 A1 | 11/2003 | Bowman, Jr. et al. | |
| 2004/0074311 A1 | 4/2004 | Lull et al. | |
| 2004/0177703 A1 | 9/2004 | Schumacher et al. | |
| 2005/0004534 A1 | 1/2005 | Lockwood et al. | |
| 2006/0144163 A1 | 7/2006 | Friberg | |
| 2006/0162466 A1 | 7/2006 | Wargo et al. | |
| 2006/0236781 A1 | 10/2006 | Ohmi et al. | |
| 2007/0193369 A1 | 8/2007 | Evans et al. | |
| 2007/0265877 A1 | 11/2007 | Rice et al. | |
| 2007/0277824 A1 | 12/2007 | Aylsworth et al. | |
| 2008/0059084 A1 | 3/2008 | Wang et al. | |
| 2008/0092891 A1 | 4/2008 | Cewers | |
| 2008/0105259 A1 | 5/2008 | de Silva et al. | |
| 2009/0038615 A1 | 2/2009 | Bradley | |
| 2009/0093774 A1 | 4/2009 | Wang et al. | |
| 2009/0113996 A1 | 5/2009 | Wang et al. | |
| 2009/0293634 A1 | 12/2009 | Ong | |
| 2009/0326839 A1 | 12/2009 | Rogers et al. | |
| 2010/0139660 A1 | 6/2010 | Adahan | |
| 2010/0229967 A1 | 9/2010 | Yasuda et al. | |
| 2010/0236552 A1 | 9/2010 | Kwok et al. | |
| 2010/0307490 A1 | 12/2010 | Broborg et al. | |
| 2011/0100364 A1 | 5/2011 | Faram | |
| 2011/0126834 A1 | 6/2011 | Winter et al. | |
| 2011/0126837 A1 | 6/2011 | Winter et al. | |
| 2012/0065533 A1 | 3/2012 | Carrillo, Jr. et al. | |
| 2012/0085349 A1 | 4/2012 | Tobias et al. | |
| 2012/0185102 A1 | 7/2012 | Skoglund et al. | |
| 2012/0204874 A1 | 8/2012 | Sofranko | |
| 2012/0226449 A1 | 9/2012 | Delache et al. | |
| 2012/0229272 A1 | 9/2012 | Jacob et al. | |
| 2012/0285454 A1 * | 11/2012 | Nibu | A61M 16/0066 128/204.18 |
| 2012/0318383 A1 | 12/2012 | Yasuda et al. | |
| 2013/0079667 A1 | 3/2013 | Berkcan et al. | |
| 2013/0220314 A1 | 8/2013 | Bottom | |
| 2013/0247905 A1 | 9/2013 | Miller et al. | |
| 2014/0054479 A1 | 2/2014 | Shen | |
| 2014/0066880 A1 | 3/2014 | Prince et al. | |
| 2014/0182590 A1 | 7/2014 | Platt et al. | |
| 2014/0251322 A1 | 9/2014 | Miller | |
| 2015/0096560 A1 | 4/2015 | Klenner et al. | |
| 2015/0143921 A1 | 5/2015 | Postberg et al. | |

FOREIGN PATENT DOCUMENTS

| | | |
|---|---|---|
| CN | 103041492 A | 4/2013 |
| CN | 202870631 U | 4/2013 |
| EP | 0829793 A1 | 3/1998 |
| EP | 1127583 A2 | 8/2001 |
| EP | 1658874 A2 | 5/2006 |
| EP | 2402616 A1 | 1/2012 |
| JP | S56597 A | 1/1981 |
| WO | WO-0138832 A2 | 5/2001 |
| WO | WO-2006024532 A1 | 3/2006 |
| WO | WO-2011055254 A1 | 5/2011 |
| WO | WO-2013002699 A1 | 1/2013 |

OTHER PUBLICATIONS

International Search Report and Written Opinion in PCT Application No. PCT/US2014/044441 dated Oct. 31, 2014, 12 pages.

International Search Report and Written Opinion in PCT Application No. PCT/US2014/044724 dated Oct. 21, 2014, 12 pages.

Invitation to Pay Additional Fees in PCT Application No. PCT/US2014/044743 dated Oct. 21, 2014, 7 pages.

International Search Report and Written Opinion in PCT Application No. PCT/US2014/044442 dated Nov. 3, 2014, 10 pages.

International Search Report and Written Opinion for International Application No. PCT/US2014/044737, dated May 19, 2015, 18 pages.

Invitation to Pay Additional Fees in International Application No. PCT/US2014/044737 dated Oct. 28, 2014, 7 pages.

International Search Report for International Application No. PCT/US2014/044743, dated Jan. 22, 2015, 6 pages.

International Search Report and Written Opinion for Application No. PCT/US2015/038155, dated Dec. 17, 2015, 18 pages.

Invitation to Pay Additional Fees and Partial Search Report for Application No. PCT/US2015/038155, dated Oct. 7, 2015, 7 pages.

International Search Report and Written Opinion for Application No. PCT/US2015/038157, dated Nov. 5, 2015, 12 pages.

Chinese Office Action for Application No. 201480036606.9, dated Sep. 2, 2016, 6 pages excluding translation.

Chinese Office Action for Application No. 201480037090.X, dated Sep. 26, 2016, 6 pages excluding English translation.

* cited by examiner

LOW-NOISE BLOWER

CROSS-REFERENCES TO RELATED APPLICATIONS

Not applicable.

BACKGROUND

Field

The present disclosure generally relates to gas compressors and, in particular, to a centrifugal air blower.

Description of the Related Art

Patients with respiratory injury, such as chronic respiratory failure, may be provided with a respirator to assist with their breathing or, in severe cases, take over the breathing function entirely. Respirators typically provide a flow of air, or other breathing gases, at an elevated pressure during an inhalation interval, followed by an exhalation interval where the pressurized air is diverted so that the air within the patient's lungs can be naturally expelled. The inhalation interval may be initiated upon detection of a patient's natural inhalation or by the respirator Respirators are available in a variety of sizes with different ranges of air flows and pressures that can be provided. For example, a neonatal patient will require a much lower pressure and volume of air per breath than an adult, and many conventional respirators cannot provide accurate delivery of pressurized air over this range of volumes and pressures.

In conventional respirators that use a blower to pressurize the gas provided to the patient, the blowers that are used are loud and the noise level in the patient's room is commonly 65 dB or more. This level of noise may disrupt the patient's rest and sleep as well as cause fatigue for the caregiver and may further obstruct diagnosis and monitoring of the patient by masking the natural breathing noises that provide an indication of the patient's condition.

SUMMARY

It is advantageous to provide a small, quiet blower that can accurately provide a flow of compressed gas over wide ranges of flow rate and pressure.

In certain embodiments, a blower is disclosed that has an impeller comprising an impeller plate and a plurality of blades each attached to the impeller plate. Each blade has a tip and a leading surface that comprises a first portion proximate to the tip. The first portion has a first radius that is within a range of 0.03-0.20 inch.

In certain embodiments, an impeller is disclosed that has an impeller plate having an outside edge with a first radius and a plurality of blades attached to the impeller plate. Each of the plurality of blades comprises a tip at the outside edge and a leading surface with a first portion extending from the tip and a second portion that extends from the first portion with a second radius that is within the range of 0.14-0.16 inch.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

It is advantageous to provide a relatively small, quiet blower that can accurately provide a flow of compressed gas over wide ranges of flow rate and pressure.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. In the referenced drawings, like numbered elements are the same or essentially similar. Reference numbers may have letter suffixes appended to indicate separate instances of a common element while being referred to generically by the same number without a suffix letter.

While the discussion herein is directed to the provision of compressed air as part of a medical respirator, the disclosed concepts and methods may be applied to other fields that would also benefit from a quiet, portable source of compressed air. For example, conventional leaf blowers that are commonly used to blow leaves and small garden debris into piles are quite loud and a blower of this type may be advantageous in place of the current blowers.

Figure 1:
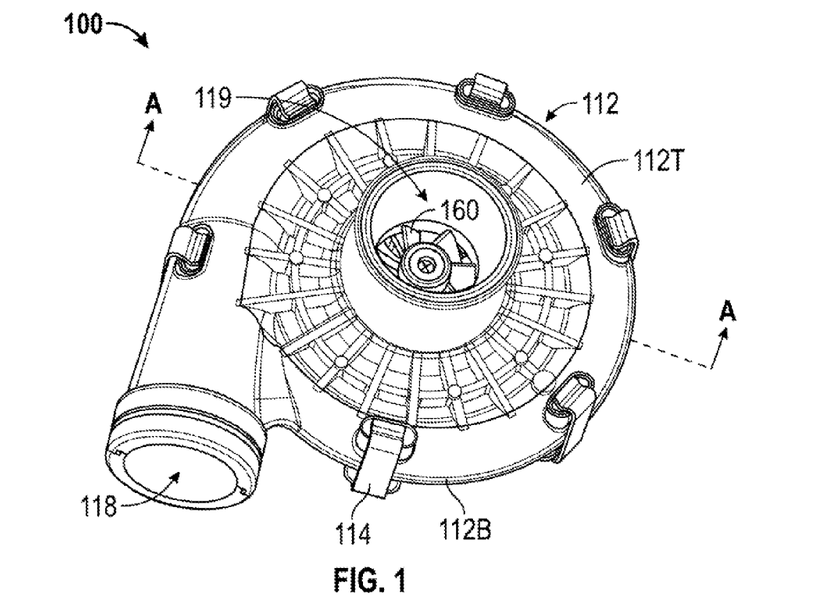
FIGS. 1-2 are top and bottom perspective views of an exemplary blower according to certain aspects of the present disclosure.
Figure 2:
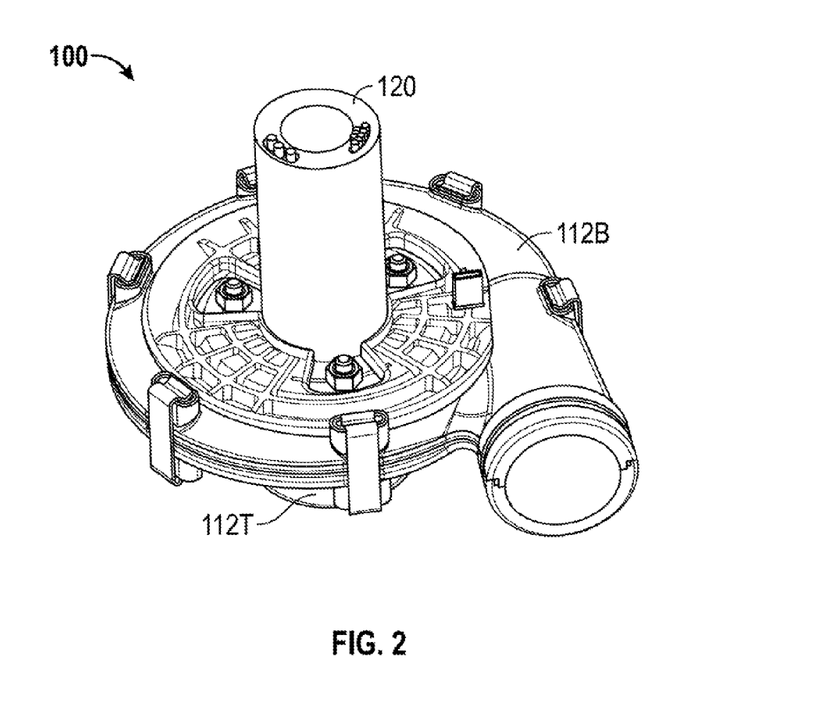

FIGS. 1-2 are top and bottom perspective views of an exemplary blower 100 according to certain aspects of the present disclosure. In the configuration of FIG. 1, the blower 100 draws in ambient air, or other gases if connected to a source of gas, through inlet 119 of housing 112. Impeller 160 may rotate at a variable speed up to 30,000 rotations per minute (rpm), for example, to centrifugally accelerate the air and provide a flow of pressurized air at outlet 118. In this embodiment, the housing 112 comprises two parts, 112T and 112B (see FIG. 3) held together with multiple clips 114. The section line A-A indicates the cross-sectional view of FIG. 7.

FIG. 2 is a perspective view of the blower 100 of FIG. 1 with the blower 100 rotated so as to make the bottom housing portion 112B visible. A motor 120 is attached to the housing 112 and the shaft of the motor (not visible in FIG. 2) passes through the housing 112 and connects to the impeller 160.

Figure 3:
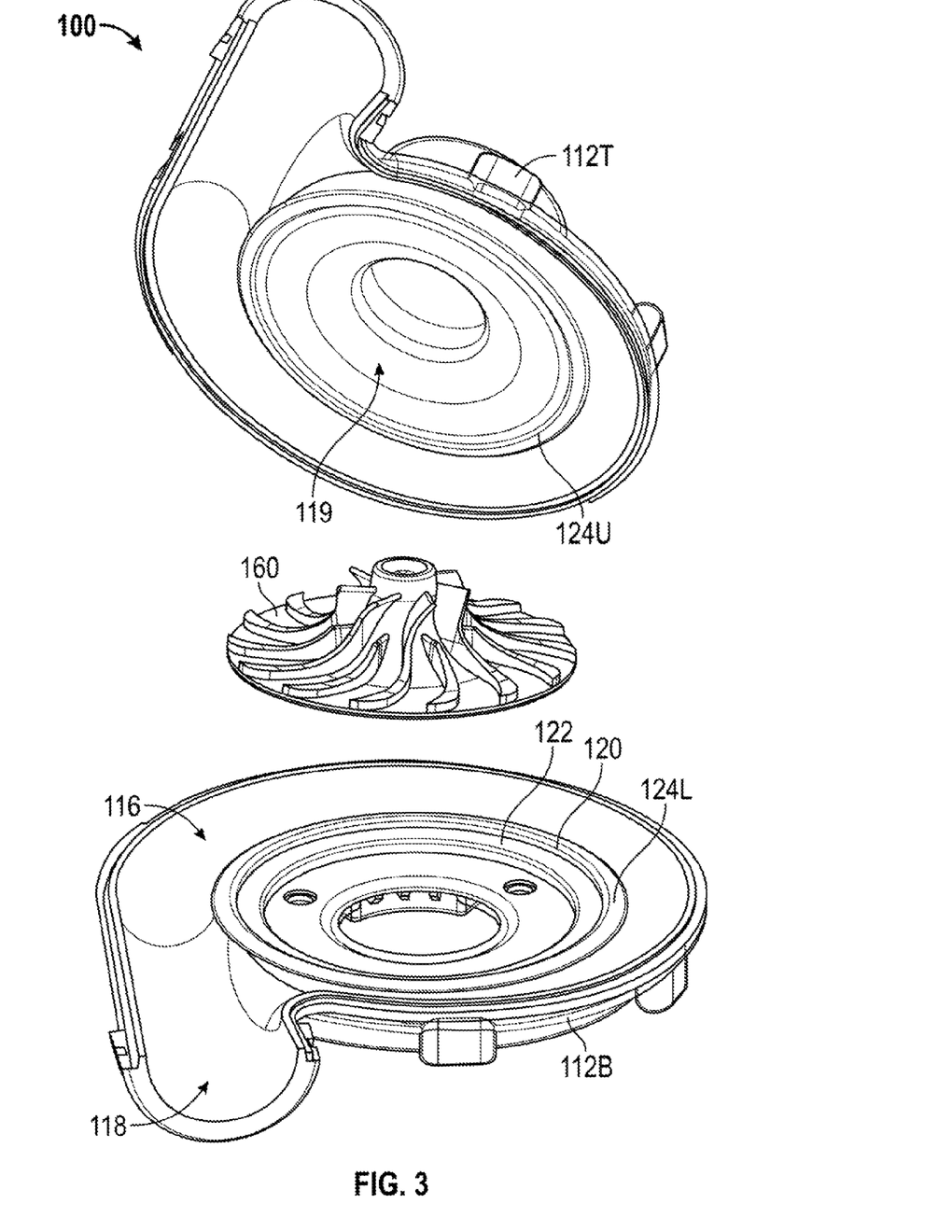
FIG. 3 is an exploded view of the blower of FIG. 1 according to certain aspects of the present disclosure.

FIG. 3 is an exploded view of the blower 100 of FIG. 1 according to certain aspects of the present disclosure. The top housing portion 112T has an impeller cavity 119. The impeller 160 is at least partially disposed within the impeller cavity 119 when the blower 100 is assembled. The housing 112 comprises a collector 116 formed when the top and bottom housing portions 112T, 112B are mated. In this example, the collector 116 is shaped as a volute having a circular cross-sectional profile along a radial plane of the housing 112, wherein the area of the profile monotonically increases as the distance around the volute from the outlet 118 decreases. In certain embodiments, the volute may have a non-circular profile. In certain embodiments, the area of the profile may be constant over a portion of the volute.

The top and bottom housing portions 112T, 112B also respectively include edges 124U, 124L that are proximate to each other when the blower 100 is assembled and surround the impeller cavity so as to cooperatively define a slot (not visible in FIG. 3) that connects the impeller cavity 119 to the collector 116. The lower housing portion 112B also includes a wall 120 and a shelf 122 adjacent to the edge 124L. This region of the blower 100 is described in greater detail with respect to FIG. 7.

Figure 4:
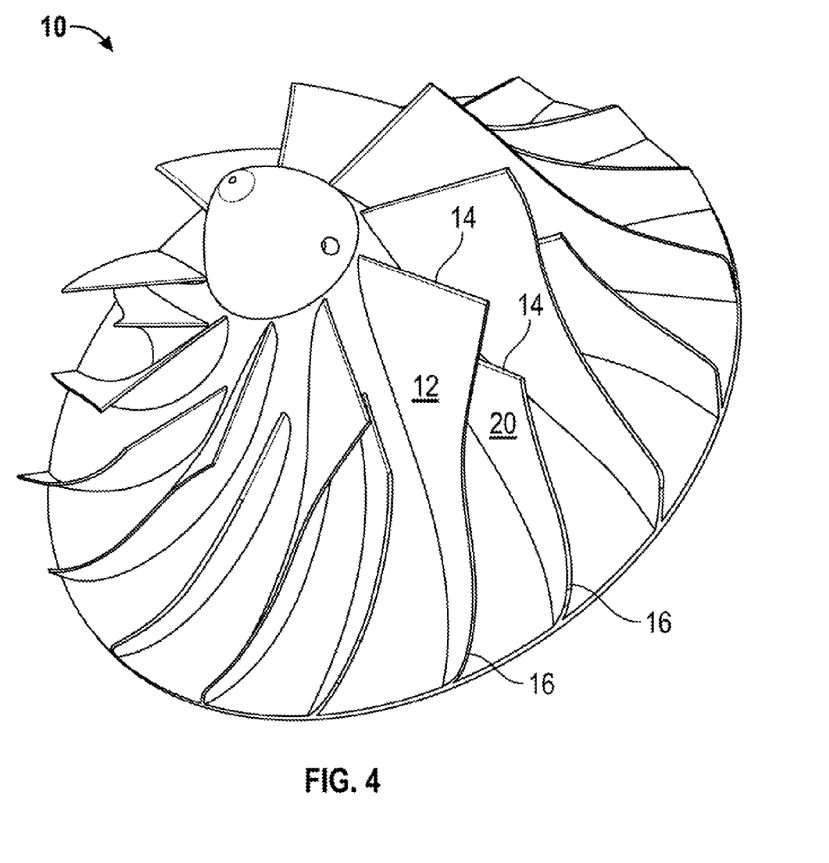
FIG. 4 is a perspective view of an exemplary impeller according to certain aspects of the present disclosure.

FIG. 4 is a perspective view of a conventional impeller 10. This impeller 10 has a plurality of vanes 12, 20 each having a leading edge 14 and a trailing edge 16, although vanes 20 are shorter than vanes 12 and are commonly referred to as "splitters." Conventional vanes 12, 20 have a three-dimensional curvature with a generally uniform thickness from leading edge 14 to trailing edge 16, with some rounding of the outside corners and filleting of the inside corners.

Figure 5:
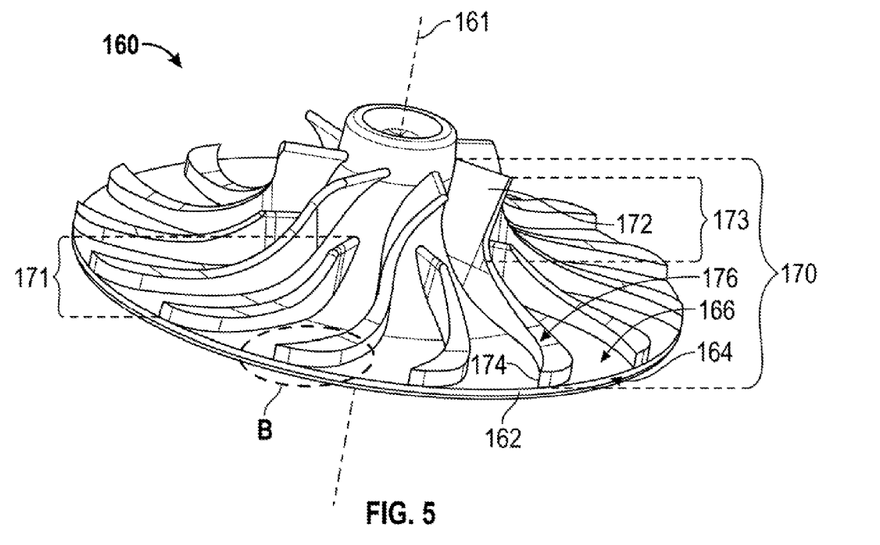
FIG. 5 is a close-up plan view of a vane tip of the impeller of FIG. 3 according to certain aspects of the present disclosure.

FIG. 5 is a perspective view of an exemplary impeller 160 according to certain aspects of the present disclosure. The impeller 160 comprises an impeller plate 162 having a shaped surface 166 and a circular outside edge 164 that are centered about an axis of rotation 161. In this embodiment, there is a set of long vanes 170 that alternate with a set of splitter vanes 171. The portion of the long vanes 170 that is not present in the splitter vanes 171 is referred to as the "inducer" 173. Each vane 170, 171 has an inlet edge 172, a tip 174 that is proximate to the outside edge 164, and a top surface 176 that is, in this example, flat in a generally circumferential direction about axis 161 while being curved in a generally radial direction. The region indicated by the dashed-line oval labeled "B" is shown in FIG. 6.

Figure 6:
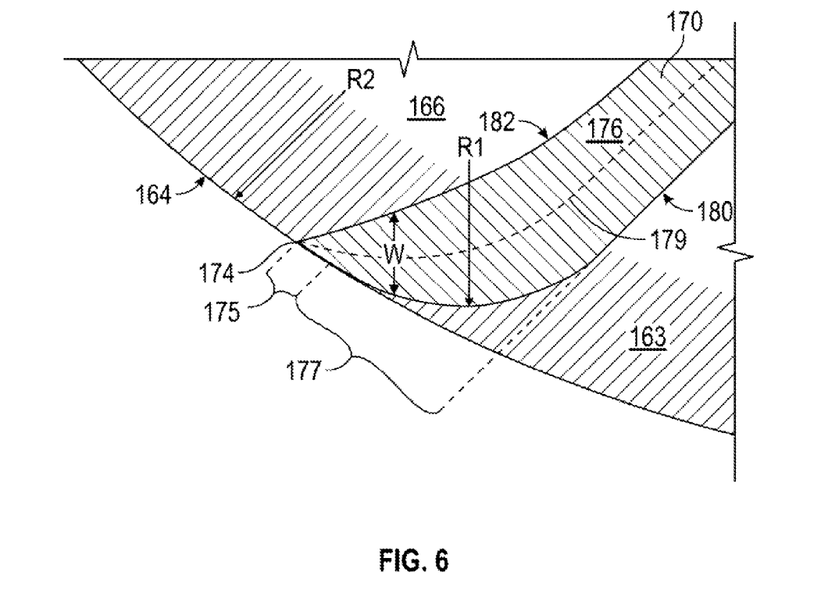
FIG. 6 is a perspective view of a conventional impeller.

FIG. 6 is a close-up plan view of a vane tip 174 of the impeller 160 of FIG. 5 according to certain aspects of the present disclosure. The example vane 170 has a leading surface 180 and a trailing surface 182 that meet at the tip 174. The leading surface 180 comprises a first portion 177 and a second portion 175. In this example, the second portion 175 extends from the tip 174 with a radius R2 that is the same radius as the outside edge 164. The first portion 177 abuts the second portion 175 and continues with a radius R1 that is smaller than R2 and larger than the radii conventionally used to round outside edges. In certain embodiments, the radius R1 may be within the range of 0.03-0.20 inch. In certain embodiments, the radius R1 may be within the range of 0.12-0.18 inch. In certain embodiments, the radius R1 may be within the range of 0.14-0.16 inch. In certain embodiments, the radius R1 may be approximately 0.15 inch.

Without being bound by theory, it is believed that the effect of the radius R1 may be to control the turbulence of the air at the tip 174 and reduce the velocity gradient in the air flow as the air leaves the impeller 160, compared to a conventional vane that abruptly ends at the outside edge with a sizable angle between the leading surface and the outside edge, as is visible in the impeller 10 of FIG. 4. By smoothing this transition over a larger area, e.g. the length of the first portion 177 and possible the second portion 175, and redirecting the air flow direction, the velocity gradient is reduced and the air flow may be less turbulent as the air leaves the impeller 160 and passes through the slot 126.

Each vane 170, 171 has a centerline 179 that is coincident with and bisects the top surface 176 between the leading and trailing surfaces 180, 182. The vanes 170, 171 have a common width W taken perpendicular to the centerline 179, wherein W varies along the centerline 179. At a common distance from the tip 174 along the centerline 179, the width W of each vane 170, 171 will be the same, for at least the length of the splitter vanes 171.

The shape and width of the vanes 170, 171 proximate to the second portion 177 may be selected to simply enable the radius to be as large as R1, compared to the constant-thickness vanes of a conventional impeller. In certain embodiments, the trailing surface 182 has a minimum radius that is greater than the radius of the first portion of the leading surface 180. In certain embodiments, the shape and location of the trailing surface 182 may be chosen to cooperate with the leading surface of the adjacent vane 170, 171 to control the pressure and/or velocity of the air flowing between the leading and trailing surfaces 180, 182.

The height of the vanes 170, 171, i.e. the distance from the shaped surface 166 to the top surface 176, varies from the inlet edge 172 and tip 174. In certain embodiments, the height is constant from the tip 174 over the first and second portions 177, 175 of the leading surface 180. In certain embodiments, the shaped surface 166 has an outside portion 163 that is proximate to the first and second portions 177, 175 of the leading surface 180. In certain embodiments, the shaped surface 166 is flat and perpendicular to the axis 16 in the outside portion 163.

Figure 7:
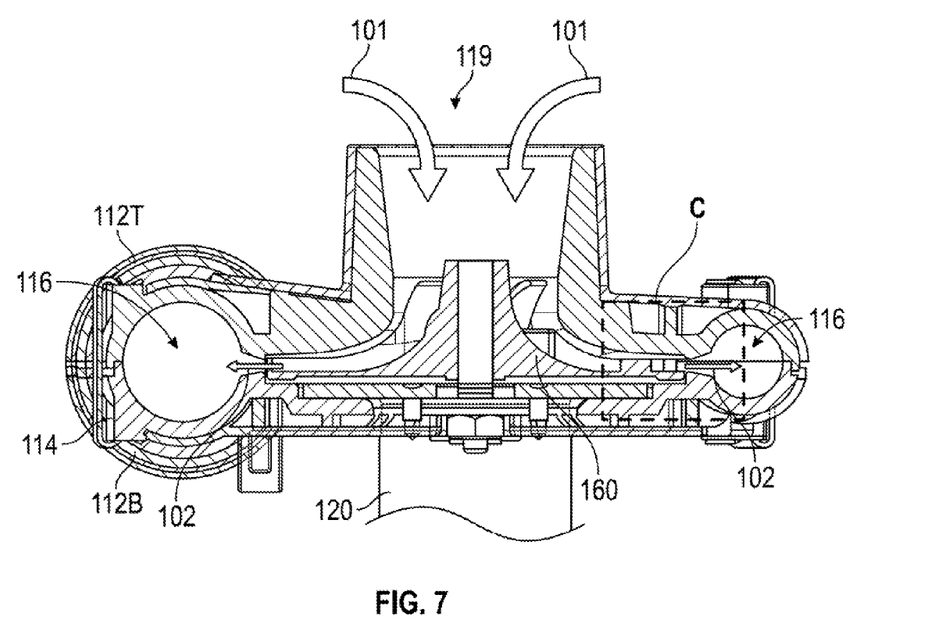
FIG. 7 is a cross-section of the blower of FIG. 1 according to certain aspects of the present disclosure.

FIG. 7 is a cross-section taken along section line A-A of the blower 100 of FIG. 1 according to certain aspects of the present disclosure. The arrows 101 and 102 respectively indicate how air is drawn in through the inlet 119 and directed by the impeller 160 into the collector 116. The motor 120 is shown in schematic form and, in this embodiment, the rotor (not shown in FIG. 7) of the motor 120 is directly connected to the impeller 160. The area indicated by the dashed-line box "C" is discussed in greater detail with respect to FIG. 8.

Figure 8:
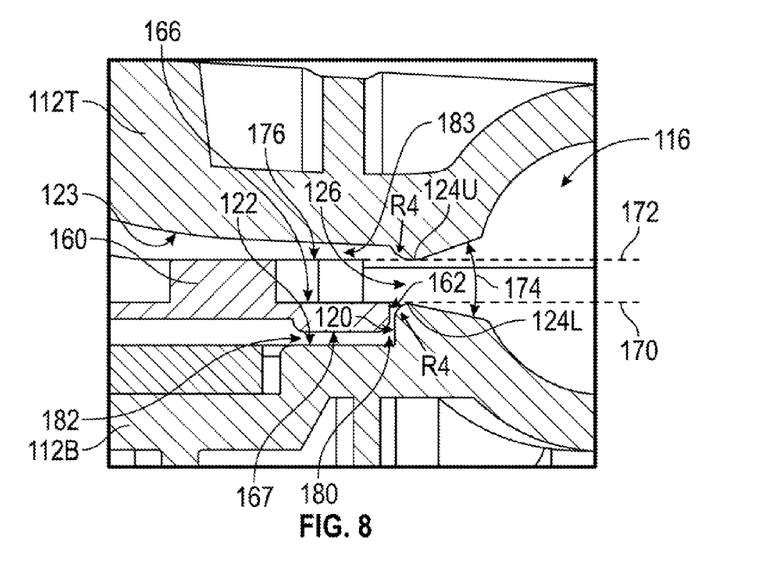
FIG. 8 is an enlarged view of a portion of FIG. 7 according to certain aspects of the present disclosure.

FIG. 8 is an enlarged view of the area C of FIG. 7 according to certain aspects of the present disclosure. The cross-section of impeller 160 shows the top surface 166, a bottom surface 167, and the outside edge 162. The upper edge 124U of the top housing portion 112T and the lower edge 124L of the bottom housing portion 112B are proximate to each other and separated by a slot 126. In this embodiment, the edges 124U and 124L both have a radius R4 on an inside corner nearest to the impeller 160, with angled surfaces that extend outward at an included angle 174 toward the collector 116. The radius R4 improves the efficiency of the nozzle formed by slot 126. The radius R4 of edges 124U and 124L induces the "Coandă effect," wherein a flowing gas will tend to follow a curved surface more readily than a sharp edge, in the gas flowing through the slot 126. This redirection of the gas flowing through the slot 126 produces a smoother transition of flow and pressure with lower loss and reduced audible noise. In certain embodiments, R4 may be within the range of 0.01-0.30 inch. In certain embodiments, R4 may be approximately 0.020 inch.

In this example, the reference line 170 is aligned with the peak of the radius R4 of lower edge 124L and the reference line 172 is aligned with the peak of the radius R4 of upper edge 124U. Thus, the slot 126 is defined by the reference lines 170, 172. In this example, the shaped surface 166 at the outside edge 162 is aligned with reference line 170, i.e. the lower edge 124L of the slot 126, and the top surfaces 176 of the plurality of blades 170, 171 are each aligned with the reference line 172, i.e. the upper edge 124U of the slot 126.

The gap between the top surface 176 and the upper inner surface 123 of the upper housing 112T is a path of potential backflow from the edge 162 of the impeller 160 toward the center. Minimizing the gap 183 between top surface 176 and the upper inner surface 123 reduces this backflow and thereby improves the pressure recovery of the blower 100. In certain embodiments, the gap 183 may be in the range of 0.002-0.150 inch when the impeller 160 is stationary relative to the housing 112. In certain embodiments, the gap 183 may be in the range of 0.005-0.050 inch. In certain embodiments, the gap 180 may be approximately 0.010 inch.

The lower edge 124L has an adjacent wall 120 with a gap 180 between the outside edge 162 and the wall 120. In certain embodiments, the gap 180 may be in the range of 0.0035-0.110 inch when the impeller 160 is stationary relative to the housing 112. In certain embodiments, the gap 180 may be in the range of 0.005-0.050 inch. In certain embodiments, the gap 180 may be approximately 0.0073 inch. In certain embodiments, the radius R2 of the outside edge 162 of the impeller 160 may increase as the rotational velocity of the impeller 160 increases and, therefore, the gap 180 may be reduced when the impeller 160 is rotating relative to the housing 112. In certain embodiments, the impeller 160 may rotate at a rotational velocity of up to 60,000 rotations per minute (rpm) relative to the housing 112 and the gap may be reduced to as little as 0.003 inch. As there will be a boundary layer (not visible in FIG. 8) attached to each of the wall 120 and the outside edge 162, reducing this gap may decrease the portion of the gap wherein airflow may go turbulent, e.g. the portion between the two boundary layers, thereby reducing the acoustic energy generated by the turbulent air.

The wall 120 connects to a shelf 122. There is a gap 182 between the bottom surface 167 of the impeller 160 and the shelf 122 of the bottom housing portion 112B. In certain embodiments, the gap 182 may be less than or equal to 0.020 inch when the impeller 160 is stationary or moving relative to the housing 112B. In certain embodiments, the gap 182 may be less than or equal to 0.050 inch. In certain embodiments, the gap 182 may be less than or equal to 0.020 inch.

Figure 9A:
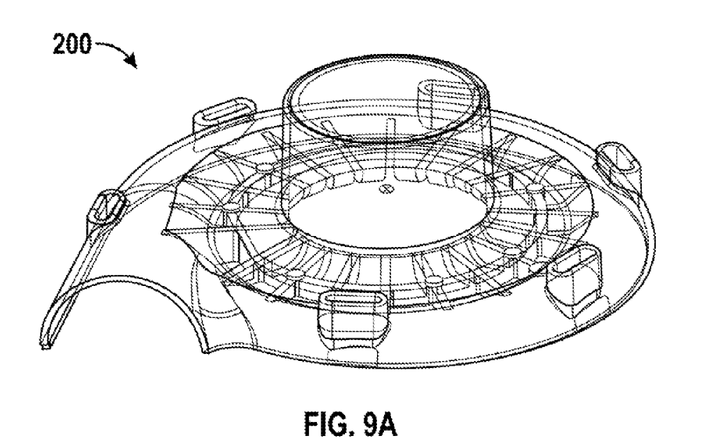
FIGS. 9A-9C are perspective views of the overmolded top housing according to certain aspects of the present disclosure.
Figure 9B:
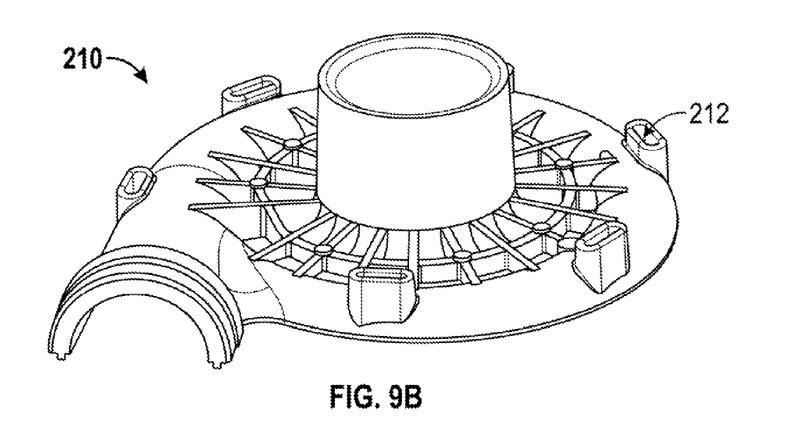
Figure 9C:
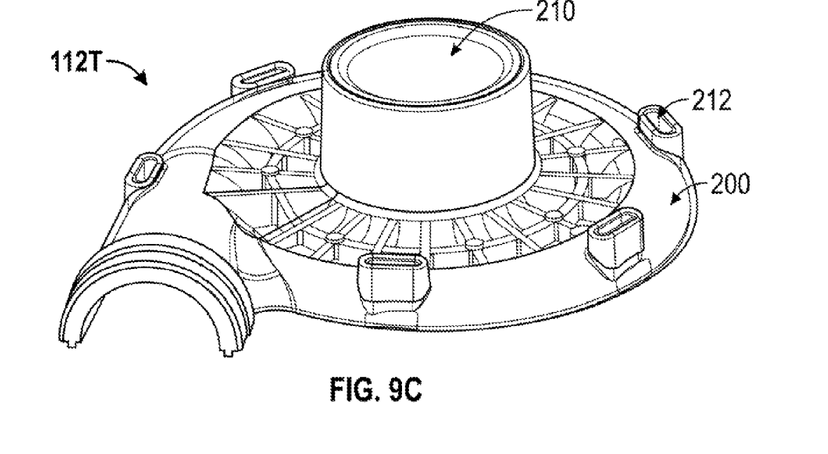

FIGS. 9A-9C are perspective views of the overmolded top housing 112T according to certain aspects of the present disclosure. FIG. 9A depicts a translucent view of a layer 200 of a sound-damping material formed so as to match the external profile of a housing shell 210 shown in FIG. 9B. In this example, the sound-damping layer 200 covers most of the external surface of the housing shell 210 with the exception of the attachment points 212 for the clips 114 (not shown in FIGS. 9A-9C). FIG. 9C shows combined top housing portion 112T with the sound-damping layer 200 on the external surface of the housing shell 210.

In certain embodiments, the sound-damping layer 200 comprises an elastomer, e.g. a silicone or rubber, having poor acoustic transmissibility. In certain embodiments, the sound-damping layer 200 may be overmolded on the housing shell 210. In certain embodiments, the sound-damping layer 200 may be applied to the housing shell 210 by one or more of the processes of transfer molding, spraying, dipping, brushing, curtain coating, or other manual or automated coating application process. In certain embodiments, the sound-damping layer 200 may comprise high-density particles, e.g. steel, that may further reduce the transmissibility of the sound-damping layer 200.

It can be seen that the disclosed embodiments of the blower may provide advantages in size, cost, performance, and reduced noise during operation. The shaping of the leading and trailing surfaces of the vanes near the outside edge of the impeller may reduce the turbulence and velocity gradient in the air flow around the tip of the vanes, thereby reducing the acoustic noise generated by the air flow. The small clearances between portions of the impeller and portions of the housing may further reduce the acoustic noise by decreasing the gaps compared to the depth of the boundary layers, thereby reducing the portion of the gap susceptible to noisy, turbulent flow.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims.

Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A blower comprising:
  an impeller comprising:
    an impeller plate; and
    a plurality of blades each attached to the impeller plate and comprising a tip and a leading surface that comprises a first portion proximate to the tip, the first portion having a first radius; and
  a housing comprising:
    an impeller cavity, wherein the impeller plate is disposed within the impeller cavity;
    a collector; and
    a slot between the impeller cavity and the collector, the slot having an upper edge and a lower edge each comprising a second radius, wherein the upper and lower edges of the slot each comprise a respective inclined surface extending from the respective edge toward the collector and an inside rounded corner nearest the impeller, the inclined surfaces disposed relative to each other at an angle within a range of 10-40 degrees such that a distance between the inclined surfaces increases as the inclined surfaces extend away from the impeller.

2. The blower of claim 1, wherein the first radius is within a range of 0.14-0.16 inch.

3. The blower of claim 1, wherein:
  the impeller plate comprises an outside edge with a third radius;
  the tip is coincident with the outside edge of the impeller plate;
  the leading surface comprises a second portion disposed between the tip and the first portion; and
  the second portion of the leading surface comprises the third radius.

4. The blower of claim 1, wherein:
  the impeller cavity further comprises an upper inner surface;
  each blade comprises a top surface; and
  a gap between the top surface at the tip of the respective blade and the upper inside surface of the impeller cavity is within a range of 0.005-0.050 inch.

5. The blower of claim 1, wherein:
  the housing comprises an inside wall that is proximate to the outside edge; and
  a gap between the inside wall and the outside edge is in a range of 0.035-0.110 inch when the impeller is stationary.

6. The blower of claim 1, wherein:
  the housing comprises a shelf;
  the impeller plate further comprises a bottom surface proximate to the outer edge and disposed over a portion of the shelf; and
  the gap between the bottom surface of the impeller plate and the shelf of the housing is less than or equal to 0.050 inch.

7. The blower of claim 1, further comprising a sound-damping layer disposed on a portion of the housing.

8. The blower of claim 7, wherein the sound-damping layer comprises a layer disposed on an external surface of the housing over the collector and impeller cavity.

9. The blower of claim 7, wherein the sound-damping layer comprising an elastomer.

10. The blower of claim 1, wherein the collector is formed as a volute.

11. The blower of claim 1, wherein the impeller is formed as a centrifugal impeller.

12. The blower of claim 11, wherein:
  the top surface of each of the plurality of blades comprises a centerline from the tip of the respective blade to an inlet end of the respective blade;
  each of the plurality of blades comprises a maximum width that is measured perpendicular to the centerline and intersects the first portion of the leading edge.

13. The blower of claim 12, wherein:
  each of the plurality of blades comprises an initial width proximate to the inlet end of the respective blade; and
  the maximum width of each blade is at least twice the initial width of the respective blade.

14. The blower of claim 1, wherein the first radius is within a range of 0.03-0.20 inches, and wherein the second radius is within a range of 0.01-0.30 inches.

15. An impeller comprising:
  an impeller plate having an outside edge with a first radius; and
  a plurality of blades attached to the impeller plate, the plurality of blades comprising a first set of blades each comprising an inducer and a second set of blades without inducers, each of the plurality of blades comprising:
    a tip at the outside edge;
    a convex leading surface having a first portion extending from the tip and a second portion extending from the first portion with a second radius; and
    a concave trailing surface that terminates at the tip and has a minimum radius that is greater than the second radius,
    wherein the blade is solid from the convex leading surface to the concave trailing surface.

16. The impeller of claim 15, wherein:
  the impeller comprises an axis of rotation;
  the impeller plate comprises a shaped surface; and
  the shaped surface comprises an outside portion proximate to the outside edge; and
  the outside portion of the shaped surface is perpendicular to the axis of rotation.

17. The impeller of claim 16, wherein:
  each of the plurality of blades comprises a top surface; and
  each top surface comprises a portion that is proximate and parallel to the outside portion of the shaped surface.

18. The impeller of claim 15, wherein the second radius is within a range of 0.14-0.16 inches.

19. An impeller comprising:
  an impeller plate having an outside edge with a first radius; and
  a plurality of blades attached to the impeller plate, each of the plurality of blades comprising:
    a tip coincident with the outside edge;
    a convex leading surface extending from the tip and comprising (i) a first portion proximate to the tip and having a second radius, and (ii) a second portion disposed between the tip and the first portion and having the first radius; and a concave trailing surface extending from the tip with a third radius, the third radius greater than the second radius, wherein the blade is solid from the convex leading surface to the concave trailing surface.

20. The impeller of claim 19, wherein each of the plurality of blades comprises a centerline and a width perpendicular to the centerline, the width varying along the centerline.

* * * * *